United States Patent
Pestronk (10) Patent No.: US 6,228,598 B1
(45) Date of Patent: May 8, 2001

(54) ANTIBODIES TO HEPARAN SULFATE GLYCOSAMINOGLYCANS IN THE DIAGNOSIS OF POLYNEUROPATHIES

(75) Inventor: Alan Pestronk, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/165,437

(22) Filed: Oct. 2, 1998

(51) Int. Cl.$^7$ .................................................. G01N 33/53
(52) U.S. Cl. ......................... 435/7.1; 436/501; 436/503; 436/506; 436/507; 436/513; 424/130.1; 424/137.1
(58) Field of Search ............................ 424/130.1, 137.1; 435/7.1; 436/501, 503, 506, 507, 513

(56) References Cited

PUBLICATIONS

Terryberry, J. W. et al., *Neurobiology of Aging*, 19(3): 205–216, May 1998.*

Fredman, P. et al., "Antibodies in sera from patients with inflammatory demyelinating polyradiculoneuropathy react with ganglioside LM1 and sulphatide of peripheral nerve myelin," *J. Neurol.* 238: 75–79 (1991).

Vriesendorp, F.J. et al., "Serum antibodies to GM1, GD1b, peripheral nerve myelin, and Campylobacterjejuni in patients with Guillain–Barre syndrome and controls: correlation and prognosis," *Ann. Neurol.* 34:130–135 (1993).

Willison, H.J. and Kennedy, P.G., "Gangliosides and bacterial toxins in Guillain–Barre syndrome," *J. Neuroimmunol* 46:105–112 (1993).

Gilburd, B. et al., "Autoantibodies to phospholipids and brain extract in patients with the Guillain–Barre syndrome: cross–reactive or pathogenic?," *Autoimmunity* 16;23–27 (1993).

Hafer–Macko, C.E. et al., "Immune attack on the Schwann cell surface in acute inflammatory demyelinating polyneuropathy," *Ann. Neurol.* 39:625–635 (1996).

Hartung, H.P. et al., "Immunopathogenesis and treatment of the Guillain–Barre syndrome–part I.," *Muscle Nerve* 18:137–153 (1995).

Ilyas, A.A. et al., "Serum antibodies to gangliosides in Guillain–Barre syndrome," *Ann. Neurol.* 23:440–447 (1988).

Kusunoki, S. et al., "No–acetylgalactosaminyl GD1a is a target molecule for serum antibody in Guillain–Barre syndrome," *Ann. Neurol.* 35:570–576 (1994).

Pestronk, A. and Choski, R., "Multifocal motor neuropathy: Serum IgM anti–GM1 ganglioside antibodies in most patients detected using covalent linkage of GM1 to ELISA plates," *Neurology* 49:1289–1292 (1997).

Shibata, S. et al., "Autoantibodies to vascular heparan sulfate proteoglycan in systemic lupus erythematosus.," *Clin. Immunol. Immunopathol.* 70:114–123 (1994).

van den Berg, L.H. et al., "Anti–GM1 antibodies in patients with Guillain–Barre syndrome," *J. Neurol. Neurosurg. Psychiat* 55:8–11 (1992).

Simone, I.L. et al., "Serum and CSF anti–GM1 antibodies in patients with Guillain–Barre syndrome and Chronic Inflammatory Demyelinating Polyneuropathy," *J. Neurol. Sci.* 114:49–55 (1993).

Burger, D. et al., "Anti–myelin–associated glycoprotein antibodies in patients with a monoclonal IgM gammopathy and polyneuropathy, and a simplified method for the preparation of glycolipid antigens," *J. Immunol. Methods* 140:31–36 (1991).

Pestronk, A. et al., "Polyneuropathy syndromes associated with serum antibodies to sulfatide and myelin–associated glycoprotein," *Neurology* 41:357–362 (1991).

Cruz, M. et al., "Antibodies to myelin–associated glycoprotein are found in cerebrospinal fluid in polyneuropathy associated with monoclonal serum IgM," *Arch. Neurol.* 48:66–70 (1991).

Connolly, A.M. et al., "High–titer selective serum anti–beta–tubulin antibodies in chronic inflammatory demyelinating polyneuropathy," *Neurology* 43:557–562 (1993).

Fillit, H. and Lahita, R., "Antibodies to vascular heparan sulfate proteoglycan in patients with systemic lupus erythematosus," *Autoimmunity* 9:159–164 (1991).

Ilyas, A.A., et al., "Antibodies to acidic glycolipids in Guillain–Barre syndrome and chronic inflammatory demyelinating polyneuropathy," *J. Neurol. Sci.* 107:111–121 (1992).

* cited by examiner

Primary Examiner—Marianne P. Allen
(74) *Attorney, Agent, or Firm*—Hamilton, Brook, Smith & Reynolds, P.C.

(57) ABSTRACT

Methods aiding in the diagnosis of certain immune-mediated, motor-sensory polyneuropathies, both chronic and acute, by assessing the amount of antibodies to heparan sulfate glycosaminoglycan, either acetylated or nonacetylated, in a test sample, are disclosed, as are kits that can be used in the methods.

20 Claims, 3 Drawing Sheets

ANTIBODIES TO HEPARAN SULFATE GLYCOSAMINOGLYCANS IN THE DIAGNOSIS OF POLYNEUROPATHIES

BACKGROUND OF THE INVENTION

Guillain-Barré syndrome (GBS) is an acute, immune-mediated, motor-sensory polyneuropathy (AIP) that typically has evidence of demyelination on electrodiagnostic or pathological studies (Asbury, A. K., and McKhann, G. M., *Ann. Neurol* 41:287–288 (1997); Asbury, A. K., and Comblath, D. R., *Ann. Neurol.* 27suppl:S21-4 (1990)). Other AIP syndromes have selective motor (McKhann, G. M. et al., *Ann. Neurol.* 33:333–342 (1993)), cranial nerve (Fisher, M., *N. Engl. J. Med.* 255:57–65 (1956)), or axonal involvement (Feasby, T. E. et al., *Brain* 109:1115–1126 (1986)). In acute motor axonal neuropathy (AMAN) (Kornberg, A. J. and Pestronk, A., *Muscle Nerve* 17:100–104 (1994)) and Miller-Fisher syndrome (Chiba, A. et al., *Ann. Neurol.* 31:677–679 (1992)), antibodies directed against neural antigens, such as glycolipids, have been reported in 30% to 90% of patients; however, serum antibodies, with some disease specificity and directed against purified neural antigens, have not been consistently identified in most motor-sensory GBS syndromes with demyelinating features (Hartung, H. P. et al., *Muscle Nerve* 18:137–153 (1995); Rostami, A. M., *Spring. Semin. Immunopathol.* 17:29–42 (1995); Vriesendorp, F. J. et al., *Ann. Nerol.* 34:130–135 (1993); Ilyas, A. A. et al., *Ann. Neurol.* 23:440–447 (1988); Willison, H. J. and Kennedy, P. G., *J. Neuroimmunol.* 46:105–112 (1993)).

Because polyneuropathies are potentially treatable, correct identification of a patient's particular polyneuropathies is important. Methods of diagnosing such polyneuropathies based on specific disease-related criteria would facilitate identification of treatable disease and expedite commencement of treatment.

SUMMARY OF THE INVENTION

The current invention pertains to methods for diagnosing, in an individual, certain immune-mediated, motor-sensory polyneuropathies (MSP), particularly Guillain-Barré syndrome (GBS); chronic demyelinating polyneuropathy having an acute, GBS-like onset; multifocal motor neuropathy (MMN); polyneuropathy with serum IgM M protein; or polyneuropathy with antibodies to myelin-associate glycoprotein (MAG). The methods include assaying a test sample of bodily fluid, blood, serum or other tissue from an individual for the presence of antibodies, such as IgM or IgG antibodies, that bind to a heparan sulfate glycosaminoglycan or to an acetylated heparan sulfate glycosaminoglycan. In the methods, a heparan sulfate glycosaminoglycan sample, which can include a protein having a heparan sulfate glycosaminoglycan chain or heparan sulfate glycosaminoglycan that is not associated with a protein, and which can include acetylated heparan sulfate glycosaminoglycan or non-acetylated heparan sulfate glycosaminoglycan, is contacted with the test sample. The amount of antibody that binds to the heparan sulfate glycosaminoglycan is then assessed and compared to a reference amount, or to the amount of anti-heparan sulfate glycosaminoglycan antibody in at least one negative control sample of a comparable bodily fluid or tissue. The presence of MSP is indicated by an amount of anti-heparan sulfate glycosaminoglycan antibody that is greater than a reference amount, or by an amount of anti-heparan sulfate glycosaminoglycan antibody that is significantly greater (e.g., that is at least three standard deviations greater) in the test sample than in the negative control sample(s). In a preferred embodiment, the titer of the antibody that binds to the heparan sulfate glycosaminoglycan is assessed and compared to the titer of anti-heparan sulfate glycosaminoglycan antibody in a negative control sample of a comparable bodily fluid or tissue. If titer is used, a titer of IgM antibody in the test sample that is at least about 5,000 greater than the titer in a negative control sample, or a titer of IgG antibody in the test sample that is at least about 12,000 greater than the titer in a negative control sample, is indicative of the presence of the immune-mediated, motor-sensory polyneuropathy (MSP).

The methods of the invention use disease-specific criteria to identify the presence of certain immune-related motor-sensory polyneuropathies, and thus allow identification of disease even in the presence of varying clinical manifestations of the disease. Identification of the particular disease allows early intervention for treatment of disease and appropriate management of disease symptoms.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention pertains to methods for the diagnosis of certain immune-mediated, motor-sensory polyneuropathies (MSP), such as Guillain-Barré Syndrome (GBS) or M-protein related neuropathies, based on the presence of antibody directed toward a heparan sulfate glycosaminoglycan.

Pathological studies of peripheral nerve in Guillain-Barré Syndrome (GBS) with demyelinating features suggest that the Schwann cell surface, or its basal lamina, may be involved early in the disease course (Hafer-Macko, C. E. et al., *Ann. Neurol.* 39:625–635 (1996)). Proteoglycans are a major component of proteins on the cell surface (Hardingham, T. E. and Fosang, A. J., *FASEB J.* 6:861–870

(1992)) and in the basal lamina (Timpl, R., *EXS* 70:123–144 (1994)). They are composed of a core protein and one or more classes of carbohydrate moieties, glycosaminoglycans (GAG) (Bhavanandan, V. P., and Davidson, E. A., "Proteoglycans: Structure, Synthesis, Function" in *Glycoconjugates: Composition, Structure, and Function* (Allen, J. J. and Kisailus, E. C., eds), New York: Marcel Dekker, Inc., 167–202 (1992)).

The results of previous studies of serum antibodies to purified neural antigens in MSP have varied according to testing methodology and patient population. In some series, antibodies were detected only in very small subpopulations of GBS (Ilyas, A. A. et al., *Ann. Neurol.* 23:440–447 (1988); Kornberg, A. J. et al., *Ann Neurol.* 35:234–237 (1994)). Studies detecting a high prevalence of antibodies often either included both axonal and demyelinating forms of AIP (Kusonoki, S. et al., *Ann. Neurol.* 35:570–576 (1994); van den Berg, L. H. et al., *J. Neurol. Neurosurg. Psychiat.* 55:8–11 (1992)), or used methodology that measured titers that are low enough to lack specificity for AIP and also to be present in 3% to 20% of control patients (Fredman, P. et al., *J. Neurol.* 238:75–79 (1991); Gilburd, B. et al., *Autoimmunity* 16:23–27 (1993)).

As described herein, the presence of high titers of IgM or IgG antibodies to a heparan sulfate glycosaminoglycan correlates with the presence of certain MSP, including GBS and serum M-protein related neuropathies, in individuals. Heparan sulfate glycosaminoglycans (GAGs) are found in many tissues (Hardingham, T. E., and Fosang, A. J., *FASEB J.* 6:861–870 (1992)). Some are located in connective tissue and basal lamina, while others are moieties of surface proteins that are either integral to membranes, or extracellular, anchored to the cell by a glycosylphosphatidylinositol linkage. The carbohydrate structure of GAGs varies markedly among different tissues and proteoglycans, with differing patterns of sulfation, carboxyl groups, and N-acetylation on uronic acid or other carbohydrate structures. Heparan sulfates, as components of proteoglycans, probably play important roles in cell-cell interactions (Hardingham, T. E., and Fosang, A. J., *FASEB J.* 6:861–870 (1992)). Heparan sulfate proteoglycans have been identified in the nervous system (Watanabe, K. et al., *J. Cell Biol.* 130:1207–1218(1995); Stipp, C. S. et al., *J. Cell Biol.* 124:149–160(1994); Margolis, R. K., and Margolis, R. U., *Experientia* 49:429–446 (1993)); concentrated at neuromuscular junctions (Peng, H. B. et al., *J. Neurosci.* 15:3027–3038 (1995); Cole, G. J., and Halfter, W., *Perspect. Develop. Neurobiol.* 3:359–371 (1996)), and in Schwann cells as an externally exposed plasma membrane component (Mehta, H. et al., *J. Cell Biol.* 101:660–666 (1985); Carey, D. J. and Todd, M. S., *J. Biol. Chem.* 261:7518–7525 (1986); Carey, D. J. and Stahn, R. C., *J. Cell Biol.* 111:2053–2062 (1990)). They also play a role in the development of myelination (Obremski, V. J. and Bunge, M. B., *Develop.Biol.* 168:124–137 (1995)). The external surface of, or basement membrane around, myelinated axons appears to be a target of humoral immune mechanisms in demyelinating forms of GBS, as complement deposition in this region of peripheral nerves has been demonstrated early in the course of GBS (Hafer-Macko, C. E. et al., *Ann. Neurol.* 39:625–635 (1996)).

In particular, high titers of IgM or IgG to heparan sulfate glycosaminoglycans occurred in 34% of patients with classical Guillain-Barré syndrome (GBS) in similar frequencies in patients from three different geographic regions (the United States, China and Australia). Anti-heparan sulfate glycosaminoglycan antibodies also occurred in 19% of patients with chronic demyelinating polyneuropathy (CIDP) who had a history of an acute, GBS-like onset of disease, and not in patients with CIDP without such an acute onset of disease; in 14% of patients with multifocal motor neuropathy (MMN); in 25% or patients with a polyneuropathy and serum IgM M-protein of undefined specificity; and in 33% of patients having a polyneuropathy with antibodies to myelin-associated glycoproteins (MAG). Anti-heparan sulfate glycosaminoglycan antibodies were infrequent in control groups of patients (1%), in patients with acute motor axonal neuropathy (AMAN, 4%), and were not found in patients with the central demyelinating disorder, multiple sclerosis. Anti-heparan sulfate glycosaminoglycan antibodies were very unusual overall ($p < 0.001$) in other patients with defined diagnoses without demyelinating neuropathies (0%).

As a result of this discovery, methods are now available for diagnosing certain immune-mediated, motor-sensory polyneuropathies, including certain acute and chronic motor-sensory polyneuropathies, by assaying a test sample to detect the amount of antibody present, if any, that binds to a heparan sulfate glycosaminoglycan.

In the methods of the invention, a heparan sulfate glycosaminoglycan sample is used. The term, "heparan sulfate glycosaminoglycan sample," as used herein, can be a sample containing heparan sulfate glycosaminoglycan as a glycosaminoglycan side chain of a protein or peptide (e.g., a protein modified with a heparan sulfate glycosaminoglycan chain); alternatively, the heparan sulfate glycosaminoglycan sample can contain the heparan sulfate glycosaminoglycan that is not associated with a protein or peptide. If desired, some or all of the heparan sulfate glycosaminoglycan in the heparan sulfate glycosaminoglycan sample can be acetylated.

The heparan sulfate glycosaminoglycan sample is contacted with a test sample from an individual, such as an individual who is suspected of having a polyneuropathy. The test sample can comprise blood, serum, cerebrospinal fluid, urine, nasal secretion, saliva, or any other bodily fluid or tissue. Alternatively, the test sample can comprise antibodies isolated from a sample of bodily fluid or tissue from the individual. If the sample is isolated antibodies, the isolated antibodies can include all types of antibodies; alternatively, one or more types of antibodies (e.g., IgM or IgG antibodies, IgG antibodies, IgM and IgG antibodies) can be isolated. In a preferred embodiment, the test sample is a serum sample from the individual.

Contact of the heparan sulfate glycosaminoglycan sample with the test sample from the individual results in a "contacted sample," which is a mixture of heparan sulfate glycosaminoglycan sample and the test sample. The contacted sample is maintained under appropriate conditions to allow binding of any anti-heparan sulfate glycosaminoglycan antibody that may be present in the sample to the heparan sulfate glycosaminoglycan. The terms, "anti-heparan sulfate glycosaminoglycan antibody" or "anti-heparan sulfate glycosaminoglycan autoantibody", as used herein, refer to antibody that specifically binds to heparan sulfate glycosaminoglycan (either acetylated, non-acetylated, or both).

In one embodiment of the invention, the amount of anti-heparan sulfate glycosaminoglycan antibodies, if any, that have bound to the heparan sulfate glycosaminoglycan in the contacted sample, is compared to a reference amount. The term, "reference amount," as used herein, refers to an amount of anti-heparan sulfate glycosaminoglycan antibodies that correlates with a diagnosis of an immune-mediated, motor-sensory polyneuropathy (MSP) selected from the group consisting of Guillain-Barré syndrome (GBS); chronic demyelinating polyneuropathy having an acute, GBS-like onset; multifocal motor neuropathy (MMN); polyneuropathy with serum IgM M-protein; or polyneuropathy with antibodies to myelin-associate glycoprotein (MAG). A reference amount can be determined, for example, by comparing amounts of anti-heparan sulfate glycosaminoglycan antibodies in contacted samples from individuals known to have an immune-mediated, motor-sensory polyneuropathy, with amounts of anti-heparan sulfate glycosaminoglycan antibodies in contacted samples from individuals known not to have the MSP (e.g., a "negative control sample" as described below), and determining what amount of antibody correlates with disease. For example, in one embodiment, a "reference amount" can be an amount of anti-heparan sulfate glycosaminoglycan antibody in the test sample that statistically is significantly greater than the amount of anti-heparan sulfate glycosaminoglycan antibody in comparable control sample(s), such as an amount that is at least about three standard deviations above the amount of anti-heparan sulfate glycosaminoglycan antibody in comparable control samples.

The amount of different types of antibodies (i.e., a sum including the amount of more than one type of antibody) can be compared to the reference amount; alternatively, the amount of one particular type of antibody (e.g., the amount of IgA, IgD, IgE, IgM or IgG antibody) can be compared to the reference amount. In a preferred embodiment, the antibody is IgM or IgG antibody. The reference amount is an amount of the same type of antibody as the antibody assessed in the contacted sample: for example, if the sum of the amount of different types of antibodies (i.e., including more than one type of antibody) for the contacted sample is compared to the reference amount, the sum of the amount of those types of antibodies is also used for the reference amount. If the amount of one particular type of antibody (e.g., the amount of IgM or IgG antibodies) in the contacted sample is compared with the reference amount, the amount of that type of antibodies is also used for the reference amount. The presence of an amount that is equal to, or greater than, the reference amount correlates with a diagnosis of an immune-mediated, motor-sensory polyneuropathy (MSP) selected from the group consisting of Guillain-Barré syndrome (GBS); chronic demyelinating polyneuropathy having an acute, GBS-like onset; multifocal motor neuropathy (MMN); polyneuropathy with serum IgM M-protein; or polyneuropathy with antibodies to myelin-associate glycoprotein (MAG).

In another embodiment of the invention, the contacted sample is assayed to determine the amount of anti-heparan sulfate glycosaminoglycan antibodies, if any, that have bound to the heparan sulfate glycosaminoglycan. The assay can determine an amount that is the sum of the amount of different types of antibodies (i.e., including more than one type of antibody); alternatively, the assay can determine the amount of one particular type of antibody (e.g., the amount of IgA, IgD, IgE, IgM or IgG antibody). In a preferred embodiment, the contacted sample is assayed to determine the amount of IgM or IgG antibody.

The amount of anti-heparan sulfate glycosaminoglycan antibody in the contacted sample is compared with the amount of anti-heparan sulfate glycosaminoglycan antibody in at least one comparable negative control sample (i.e., a sample from an individual who is not afflicted by an immune-mediated, motor-sensory polyneuropathy). The negative control sample can be a sample from any individual who is not afflicted with an immune-mediated, motor-sensory polyneuropathy. It is not necessary that the negative control sample be from an individual who is free of disease: for example, the negative control sample can be a sample from an individual who has another neuropathy, such as multiple sclerosis. A "comparable" negative control sample is a sample of the same type of body fluid or tissue as the test sample; alternatively, if the test sample is antibodies isolated from a sample of fluid or tissue, the comparable negative control sample is a sample of antibodies isolated from the same type of bodily fluid or tissue. More than one control sample can be used. The assay of the negative control sample determines the same type of antibody as the assay of the contacted sample: for example, if the sum of the amount of different types of antibodies (i.e., including more than one type of antibody) is detected for the contacted sample, the sum of the amount of those types of antibodies is also determined for the negative control sample. If the assay determines the amount of one particular type of antibody (e.g., the amount of IgM or IgG antibodies) in the contacted sample, the amount of that type of antibodies is also determined for the negative control sample. In a preferred embodiment, more than one control sample can be used.

In one particular embodiment of the invention, the titer of anti-heparan sulfate glycosaminoglycan antibodies in the test sample is compared to the titer of anti-heparan sulfate glycosaminoglycan antibodies present in a comparable negative control sample(s). Antibody titer can be determined by a variety of methods using standard techniques, including enzyme-linked immunosorbent assay (ELISA) or other solid phase immunoassays, radioimmunoassay, nephelometry, electrophoresis, immunofluorescence, Western blot (immunoblot), or other methods (see Ausubel, F. M. et al., eds., Current Protocols in Molecular Biology, John Wiley & Sons, including supplements through 1997, especially units 11.2 (ELISA) and 11.16 (Determination of Specific Antibody Titer)). In a preferred embodiment, the titer is determined by ELISA; in a particularly preferred embodiment, the heparan sulfate glycosaminoglycan is attached to a solid support, in a manner that optimizes antibody binding to carbohydrate epitopes, such as by use of Nunc CovaLink NH microwell plates (see, e.g., attorney docket number WU97-01, U.S. patent application Ser. No. 08/885,977 filed Jun. 30, 1997, the entire teachings of which are incorporated herein by reference).

Typically, the amount of antibody that binds to the heparan sulfate glycosaminoglycan sample can be determined using a detector antibody that binds to the anti-heparan sulfate glycosaminoglycan antibody. Titers of anti-heparan sulfate glycosaminoglycan antibodies are calculated from the amount of detector antibody bound to the anti-heparan sulfate glycosaminoglycan antibody, using standard conversion algorithms. For example, if the detector antibody comprises horseradish peroxidase, titers of antibody can be calculated as set forth in Pestronk et al. (*Ann. Neurol.* 27):316–326 (1990)). In a preferred embodiment of the invention, the titer of anti-heparan sulfate glycosaminoglycan IgM or IgG antibodies in the test sample is compared to the titer of anti-heparan sulfate glycosaminoglycan IgM or IgG antibodies present in at least one comparable negative control sample.

The presence of an amount of anti-heparan sulfate glycosaminoglycan antibody in the test sample that is significantly greater than the amount of anti-heparan sulfate glycosaminoglycan antibody in a comparable control sample (s), correlates with a diagnosis of an immune-mediated, motor-sensory polyneuropathies (MSP), selected from the group consisting of Guillain-Barré syndrome (GBS); chronic demyelinating polyneuropathy having an acute, GBS-like onset; multifocal motor neuropathy (MMN); polyneuropathy with serum IgM M-protein; or polyneuropathy with antibodies to myelin-associate glycoprotein (MAG). In a preferred embodiment, an amount of anti-heparan sulfate glycosaminoglycan antibody in the test sample that is "significantly greater" is an amount that is at least about three standard deviations above the amount of anti-heparan sulfate glycosaminoglycan antibody in comparable control samples. For example, if the titer of both IgM and IgG antibody is measured, an amount of the combination of anti-heparan sulfate glycosaminoglycan IgM antibody and anti-heparan sulfate glycosaminoglycan IgG antibody that is equal to, or greater than, three standard deviations above the amount of the combination of anti-heparan sulfate glycosaminoglycan IgM antibody and anti-heparan sulfate glycosaminoglycan IgG antibody in comparable control samples is "significantly greater" and therefore correlates with MSP. In another example, if titer is used, a titer of anti-heparan sulfate glycosaminoglycan antibody, particularly anti-heparan sulfate glycosaminoglycan IgM antibody, in the test sample that is equal to, or greater than, three standard deviations above the titer of anti-heparan sulfate glycosaminoglycan antibody in comparable control samples, correlates with a diagnosis of the immune-mediated, motor-sensory polyneuropathy. In another preferred embodiment, a titer of anti-heparan sulfate glycosaminoglycan IgM antibody that is equal to, or greater than, about 5,000 above the titer of a negative control sample, or anti-heparan sulfate glycosaminoglycan IgG antibody in the test sample that is equal to, or greater than, about 12,000 above the titer of a negative control sample, correlates with a diagnosis of the immune-mediated, motor-sensory polyneuropathy (MSP). In this particularly preferred embodiment, it is generally expected that the amount of antibodies in the negative control sample will be less than 3,000. If the titer of both IgM and IgG antibody is measured, a titer of the combination of anti-heparan sulfate glycosaminoglycan IgM antibody and anti-heparan sulfate glycosaminoglycan IgG antibody that is equal to, or greater than, the amount of the combination of anti-heparan sulfate glycosaminoglycan IgM antibody and anti-heparan sulfate glycosaminoglycan IgG antibody in comparable control samples is "significantly greater" and therefore correlates with MSP. In this embodiment, it is generally expected that the combination of anti-heparan sulfate glycosaminoglycan IgM antibody and anti-heparan sulfate glycosaminoglycan IgG antibody will be equal to, or greater than, the titer of either anti-heparan sulfate glycosaminoglycan IgM antibody or anti-heparan sulfate glycosaminoglycan IgG antibody alone; preferably, the combination will be equal to, or greater than, the titer of the higher of the two alone (e.g., equal to, or greater than, 12,000 above the titer of the negative control sample).

The present invention also includes kits to be used in methods of the invention. Kits can include the following components: (1) a heparan sulfate glycosaminoglycan sample; and, optionally, (2) labeled detector antibody that binds to antibody, preferably to the anti-heparan sulfate glycosaminoglycan antibody, and even more preferably, to anti-heparan sulfate glycosaminoglycan IgM or IgG antibody. Detector antibody can comprise an antibody bound to a detectable agent, such as an enzyme, radioactive molecule, or fluorescent agent. If the detector antibody is bound to an enzyme that reacts with an added substrate to yield a colored product, such as horseradish peroxidase, the kit can also include the substrate. The heparan sulfate glycosaminoglycan sample in the kit can be adhered to a solid support.

The following Exemplification is offered for the purpose of illustrating the present invention and are not to be construed to limit the scope of this invention. The teachings of all references cited herein are hereby incorporated by reference in their entirety.

EXEMPLIFICATION: Correlation between Antibodies to Heparan Sulfate Glycosaminoglycans (GAGs) and Polyneuropathies Materials and Methods Serum Samples Serums were tested from 43 consecutive patients with motor-sensory GBS, and features of demyelination on electrodiagnostic testing, who were evaluated by the neuromuscular service at Barnes Hospital, St. Louis, Mo., United States, between 1989 and 1996. All had symmetric weakness developing over 3 to 25 days with variable degrees of distal symmetric sensory loss and met typical diagnostic criteria for GBS (Asbury, A. K., and Comblath, D. R., *Ann. Neurol.* 27 suppl: S21-4 (1990)). Electrodiagnostic finding supportive of demyelination in GBS patients in the first week of disease were abnormalities in at least two nerves, usually median, ulnar or peroneal, including: prolonged F-wave or distal latencies (greater than 150% of normal), absent F-waves in otherwise normal nerves, temporal dispersion in compound motor action potentials, or (rarely) slowed motor conduction velocities. As control samples, 401 other serums were tested; these included 126 patients examined at Washington University, St. Louis, Mo. (the United States patients), who met accepted criteria for diagnoses that included: chronic inflammatory demyelinating polyneuropathy (CIDP, 21 samples); multifocal motor neuropathy (MMN, 21 patients); amyotrophic lateral sclerosis (ALS) by World Federation of Neurology criteria (22 patients); multiple sclerosis (15 samples), systemic immune disorders without neurologic involvement (22 patients); idiopathic axonal sensory-motor polyneuropathies (19 patients); and hereditary demyelinating motor-sensory neuropathies (6 patients). Also evaluated were serums from the following groups: 1) Chinese patients with acute immune neuropathies (42 patients), including subgroups with axonal (26 patients) and demyelinating (16 patients) findings on electrophysiological studies) who were tested for IGG anti-GM1 antibodies as part of a prior study (Kornberg, A. J. et al., *Ann. Neurol.* 35:234–237 (1994)); 2) Australian patients with acute immune polyneuropathies (15 patients), to compare the results with a group from a third geographic area; 3) samples with high titer IgM antibody binding to myelin associated glycoprotein (MAG) (45 patients), confirmed by Western blot (Pestronk, A. et al., *Neurology* 44:1131–1137 (1994)); 4) a consecutive series referred to the Neuromuscular Clinical Laboratory at Washington University (173 patients) that was part of evaluations of polyneuropathies or motor system disorders; and patients (24 patients) with serum IgM M-protein but no known antigenic targets. Other than the selection of tests ordered by the referring physician, no clinical information was available for most of these 173 serums in group (4).

ELISA Antibody Assays

Serums were assayed for IgM and IgG binding to purified glycolipids (GM1 and GD1a gangliosides) and glycosaminoglycans (GAGs) (Sigma, St. Louis, Mo.), using Nunc CovaLink NH microwell plates (Nunc; Roskilde, Denmark) that optimize antibody binding to carbohydrate epitopes (Pestronk, A. and Choksi, R., *Neurology* 49:1289–1272 (1997)). Antigens are covalently linked to secondary amino groups in the wells of these plates. It has previously been shown that this methodology greatly increases the frequency of detection of IgM anti-GM1 ganglioside antibodies in MMN (Pestronk, A. and Choksi, R., *Neurology* 49:1289–1272 (1997); see also attorney docket number WU97-01, U.S. patent application Ser. No. 08/885,977, filed Jun. 30, 1997, the entire teachings of which are incorporated herein by reference). Each sample was tested for antibody binding to acetylated heparan sulfate GAGs, and to non-acetylated heparan sulfate GAGs.

GD1a was chosen as a control antigen with a prominent carbohydrate moiety that produced a test of high sensitivity and specificity for MMN in studies of anti-GM1 ganglioside antibodies using ELISA methodology that included the CovaLink plates (Pestronk, A. and Choksi, R., *Neurology* 49:1289–1272 (1997)). Similar results would probably be obtained using an alternative control antigen such as one of the other GAGs; however, blank wells, or those coated with protein, could not be used as controls due to high nonspecific serum binding to the CovaLink plates.

Heparan sulfate GAGs were purified from bovine intestine, and heparan sulfate proteoglycan from a mouse sarcoma cell line. Acetylated heparan sulfate GAGs were prepared from the heparan sulfate GAGs (Sigma, St. Louis, Mo.). Glycolipids (0.15 $\mu$g), proteoglycans (0.5 $\mu$g) and GAGs (0.5 $\mu$g) were dissolved in 100 $\mu$l of 1% N-(3-dimethylaminopropyl)-N-ethyl-carbodiimide (EDC) (Sigma), incubated in wells overnight at 4° C., and washed three times with PBS-0.05% Tween 20. Remaining binding sites in all ELISA wells were blocked with 1% human serum albumin (for IgM), or 1% normal goat serum (for IgG), in PBS (100 $\mu$l) for 4 hours at room temperature. Plates were then washed 3 times with 1% bovine serum albumin (BSA) in PBS. Subsequent steps were performed at 4° C. Between steps washing (×5) was performed using PBS with 1% BSA without detergent. All serums were tested in duplicate by adding dilutions (1:3×10$^3$ to 1:10$^6$ in PBS with 1% BSA) to wells overnight. The binding of IgM was measured using 4-hour exposure to goat anti-human IgM linked to horseradish peroxidase (HRP) (Organon Teknika-Cappel; West Chester, Pa.) in PBS with 1% BSA (1:20,000). Color was developed with 100 $\mu$l substrate buffer (0.1M citrate buffer, pH 4.5 with 0.004% $H_2O_2$ and 0.1% phenylenediamine) for 30 minutes. Optical density (OD) was determined at 450 nm. A serum antibody with a titer of X was detectable (>0.05 OD units over controls) up to a dilution of at least 1/X. The titer of selective serum IgM or IgG binding to GM1 ganglioside or GAGs was then calculated by subtracting the level of IgM binding to GD1a in the serum (Pestronk, A. and Choksi, R., *Neurology* 49:1289–1272 (1997)). High titers of selective anti-heparan sulfate binding were designated as those titers more than 3 standard deviations above the means of a separate initial series of tests in a control panel (10 ALS patients and 10 normal individual): for IgM, a high titer was a titer greater than 5,000, and for IgG, a high titer was a titer greater than 12,000.

To confirm the specificity of antibody binding to heparan sulfate, blocking experiments were performed using 3 GBS serums. Heparan sulfate was dissolved in EDC, as above, dialyzed to remove excess EDC, added (400 $\mu$g/ml) to prediluted sera, incubated for 30 minutes at 37° C. and then overnight at 4° C. The blocked serum was then added to ELISA wells, as above, to test for residual antibody binding.

Statistics

The Fisher exact test was used to calculate the significance of differences between proportions.

Results of Patient Screening

Initial Screening

Figure 1:
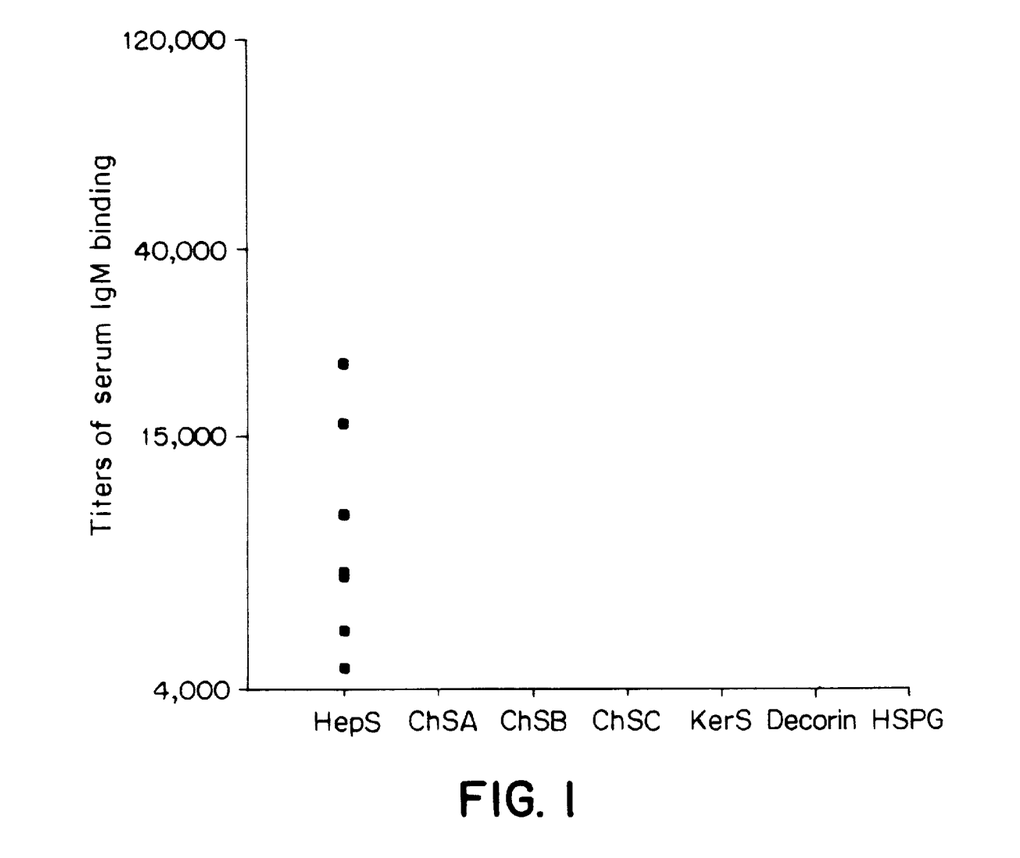
FIG. 1 is a representation of titers of serum IgM binding to glycosaminoglycans (GAGs) and proteoglycans in serums from 18 individuals with Guillain-Barré syndrome (GBS). GAGs and proteoglycans are: decorin, chondroitin A sulfate (ChSA), chondroitin B (dermatan) sulfate (ChSB), chondroitin C sulfate (ChSC), heparan sulfate (HepS), heparan sulfate proteoglycan (HSPG) and keratan sulfate (KerS).

First, 18 serums were tested from patients with GBS, for the presence of IgM and/or IgG binding to a panel of GAGs, including decorin, chondroitin A sulfate (ChSA), chondroitin B (dermatan) sulfate (ChSB), chondroitin C sulfate (ChSC), heparan sulfate (HepS), heparan sulfate proteoglycan (HSPG) and keratin sulfate (KerS). The only GAG with high titer binding by GBS serum IgM (as shown in FIG. 1) or IgG (data not shown) was heparan sulfate. There was no antibody binding to the heparan sulfate proteoglycan. Serums were then tested from a larger group of patients with GBS, other acute and chronic neuropathies, as well as controls for IgM and/or IgG binding to heparan sulfate GAGs. In these and all subsequent experiments, essentially all serums that reacted with non-acetylated heparan sulfate GAGs also reacted with acetylated heparan sulfate GAGs (data for acetylated heparan sulfate GAGs not shown).

GBS Patients

Figure 2:
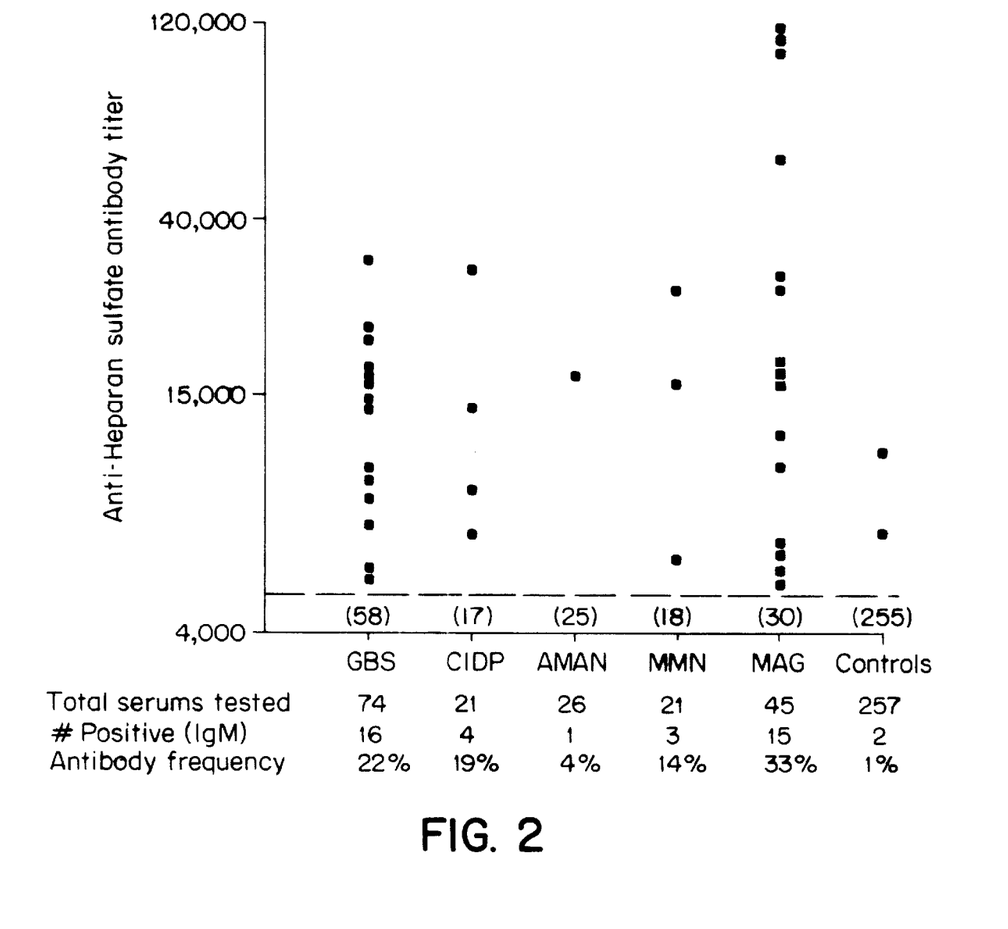
FIG. 2 is a representation of titers of serum IgM anti-heparan sulfate antibodies in serums from individuals with a variety of disorders, including Guillain-Barré Syndrome with evidence of demyelination on electrophysiological testing (GBS); chronic immune demyelinating polyneuropathy (CIDP); acute motor axonal neuropathy (AMAN); multifocal motor neuropathy (MMN); or polyneuropathy with antibodies to myelin-associated glycoprotein (MAG); as well as from serums from control individuals.
Figure 3:
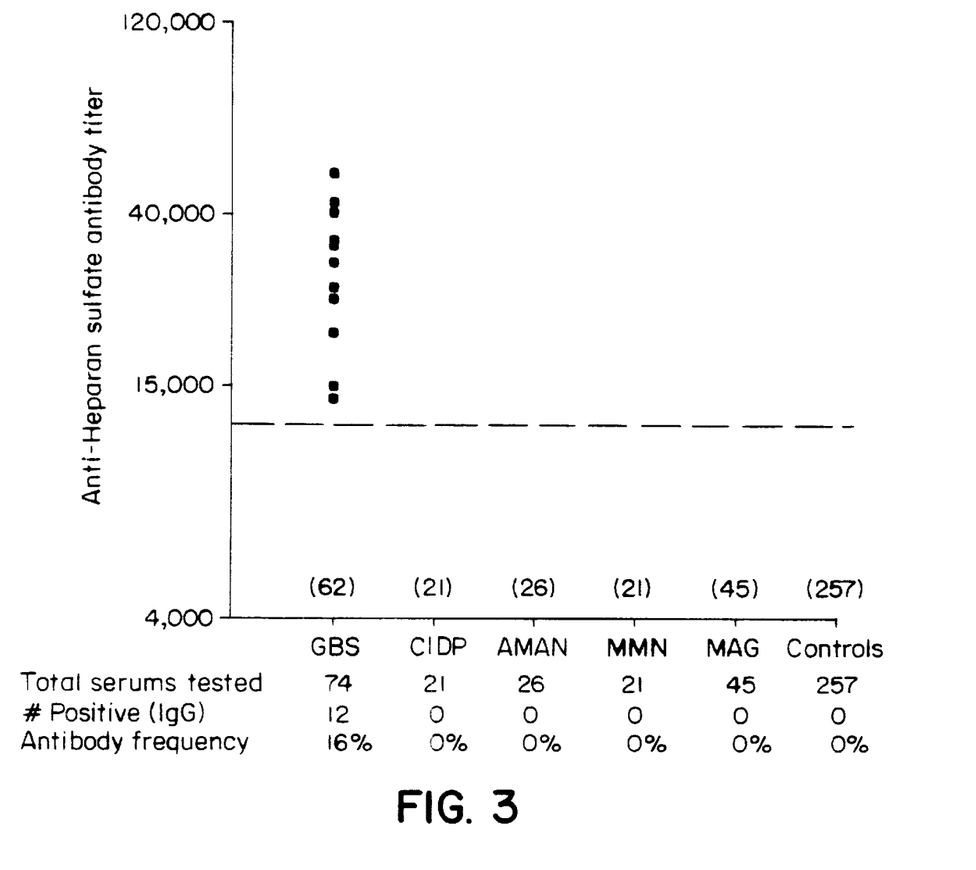
FIG. 3 is a representation of titers of serum IgG anti-heparan sulfate antibodies in serums from individuals with a variety of disorders, including GBS, CIDP, AMAN, MMN, or MAG, as well as in serums from control individuals.

Serums from 34% (20 of 59) of patients with GBS having features of demyelination had high titers of binding to heparan sulfate that was selective for IgM (24%; 14 of 59), IgG (14%; 8 of 59) or both (2 of 59). Results for IgM are shown in FIG. 2; figures in parentheses indicate numbers of serums tested with titers in the normal range (<5,000). The highest frequency of IgM anti-heparan sulfate antibodies occurred in the GBS (22%; 16 of 74 patients from the United States, China or Australia) and MAG (33%) groups. IgM antibodies were found in 24% (39 of 161) of all acquired acute and chronic demyelinating neuropathies but only in 1% (2 of 283) of other serums. Results for IgG are shown in FIG. 3; figures in parentheses indicate numbers of serums tested with titers in the normal range (<12,000). IgG anti-heparan sulfate antibodies were found in 16% of GBS patients (12 of 74) but not in the other 370 serums. Titers ranged from 5,400 to 22,000 for IgM and from 15,000 to 50,000 for IgG. Similar percentages of anti-heparan sulfate positives were found in subgroups from the United States (35%; 15 of 43) and China (31%; 5 of 16). Three untreated GBS patients with initial high anti-heparan sulfate titers of 9,000 (IgM), 28,000 (IgG) and 16,000 (IgG), had follow-up serums, obtained an average of 3 weeks later, with titers of 0. The time course of this rapid fall in titer is similar to that found for anti-GM1 antibodies in patients with AMAN (Kornberg, A. J. et al., *Ann. Neurol.* 35:234–237 (1994)) and IgG anti-GQ1b antibodies in Miller Fisher Syndrome (Kornberg, A. J., et al., *Neurology* 47:1317–1320 (1996)). Results in the group of Australian patients with GBS-like syndromes were similar to the United States and Chinese groups with 33% (5 of 15) having high titers of binding to heparan sulfate that was selective IgM (13%; 2 of 15), selective IgG (33%; 5 of 15), or both (2 of 15). These results are summarized in the Table, below.

Other Disorders

In the overall group with chronic demyelinating neuropathies, anti-heparan sulfate antibodies, all IgM, were present in 25% (22 of 87). This included 19% of patients with CIDP (4 of 21), 33% of patients with anti-MAG antibodies associated polyneuropathies (15 of 45), and 14% of patients with multifocal motor neuropathy (3 of 21). On review of the clinical records, all 4 antibody-positive CIDP patients, but none of the antibody-negative group, had an acute onset of their disease that was initially diagnosed as GBS. In other control groups, anti-heparan sulfate antibodies were infrequent, including 4% (1 of 26) of Chinese patients with acute motor neuropathies and axonal involvement, but little evidence of demyelination (AMAN), and no patients with ALS (0 of 22), multiple sclerosis (0 of 15), chronic axonal polyneuropathies (0 of 19), and non-neural immune disorders (0 of 22). In the consecutive series of serums referred to the laboratory, 1% (2 of 173) without high titer binding to MAG had high titer IgM (2 of 173) or IgG binding (0 of 173) to heparan sulfate. In the 24 patients with serum IgM M-protein, 6 showed high titer of IgM binding to heparan sulfate and to acetylated heparan sulfate. These results are summarized in the Table.

TABLE

Anti-heparan sulfate antibodies (IgM or IgG) in Different Disease Syndromes

| Disease Syndrome | GBS | CIDP | AMAN | MMN | M-P | MAG | Control |
|---|---|---|---|---|---|---|---|
| Serums tested | 74 | 21 | 26 | 21 | 24 | 45 | 257 |
| # Positive (IgM or IgG) | 25 | 4 | 1 | 3 | 6 | 15 | 2 |
| Anti-HepS Antibody Frequency | 34% | 19% | 4% | 14% | 25% | 33% | 0.8% |

GBS = Motor-sensory Guillain-Barré syndrome with evidence of demyelination on electrophysiological testing; CIDP = chronic immune demyelinating polyneuropathy; AMAN = acute motor axonal neuropathy; MMN = multifocal motor neuropathy; M-P = polyneuropathy with serum IgM M-protein; MAG = polyneuropathy with antibodies to myelin-associated glycoprotein; HepS = heparan sulfate.

Other Antibodies

There was no relationship between the presence of anti-heparan sulfate and anti-GM1 ganglioside antibodies. IgG anti-GM1 ganglioside antibodies were rare in the groups of patients with demyelinating neuropathies in which heparan sulfate antibodies were common, including all GBS (3%; 2 of 74), the subgroup of United States GBS patients (0%; 0 of 43), CIDP (0%; 0 of 21), and anti-MAG syndromes (0%; 0 of 45). In contrast, as previously reported ( Kornberg, A. J. et al., *Ann. Neurol.* 35:234–237 (1994); Pestronk, A. And Choksi, R., *Neurology* 49:1289–1272 (1997)), anti-GM1 ganglioside antibodies were relatively frequent in Chinese patients with acute motor neuropathies and axonal involvement (35%; 9 of 26). IgM anti-GM1 ganglioside antibodies were frequent in MMN patients (86%; 18 of 21) but less common in other groups, including all GBS (9%; 7 of 74), the subgroup of United States GBS patients (5%; 2 of 43), CIDP (5%; 1 of 21) and MAG serums (0%; 0 of 45). Neither anti-GD1a nor anti-MAG antibodies were present in any of the GBS serums.

Blocking Experiments

Heparan sulfate (400 μg/ml) in EDC blocked all specific antibody binding to heparan sulfate by serum IgM from 3 patients with GBS. It had no effect on the binding of an anti-chondroitin C IgM antibody to chondroitin C sulfate in ELISA wells.

Those skilled in the art will know, or be able to ascertain, using no more than routine experimentation, many equivalents to the specific embodiments of the invention described herein. These and all other equivalents are indented to be encompassed by the following claims.

What is claimed is:

1. A method of diagnosing in an individual the presence of at least one immune-mediated, motor-sensory polyneuropathy selected from the group consisting of: Guillain-Barré syndrome, chronic demyelinating polyneuropathy having an acute, Guillain-Barré syndrome-like onset, multifocal motor neuropathy, polyneuropathy with serum IgM M-protein, and polyneuropathy with antibodies to myelin-associated glycoprotein, the method comprising the steps of:

a) contacting a heparan sulfate glycosaminoglycan sample with a test sample from the individual, under conditions that allow antibodies, if present, to bind to heparan sulfate glycosaminoglycan, thereby generating a contacted sample; and b) comparing the amount of anti-heparan sulfate glycosaminoglycan antibody in the contacted sample with a reference amount, wherein the reference amount is an amount of anti-heparan sulfate glycosaminoglycan antibody that is at least about three standard deviations greater than the amount of anti-heparan sulfate glycosaminoglycan antibody in comparable negative control samples, wherein an amount of anti-heparan sulfate glycosaminoglycan antibody in the contacted sample that is equal to, or greater than, the reference amount, is indicative of the presence of at least one immune-mediated, motor-sensory polyneuropathy selected from the group consisting of: Guillain-Barré syndrome, chronic demyelinating polyneuropathy having an acute, Guillain-Barré syndrome-like onset, multifocal motor neuropathy, polyneuropathy with serum IgM M-protein, and polyneuropathy with antibodies to myelin-associated glycoprotein.

2. The method of claim 1, wherein the amount of the anti-heparan sulfate glycosaminoglycan antibody comprises an amount of antibodies that comprise IgM or IgG antibodies.

3. The method of claim 1, wherein the anti-heparan sulfate glycosaminoglycan antibody is IgM antibody.

4. The method of claim 1, wherein the heparan sulfate glycosaminoglycan sample comprises acetylated heparan sulfate glycosaminoglycan.

5. A method of diagnosing in an individual the presence of at least one immune-mediated, motor-sensory polyneuropathy selected from the group consisting of: Guillain-Barré syndrome, chronic demyelinating polyneuropathy having an acute, Guillain-Barré syndrome-like onset, multifocal motor neuropathy, polyneuropathy with serum IgM M-protein, and polyneuropathy with antibodies to myelin-associated glycoprotein, the method comprising the steps of:

a) contacting a heparan sulfate glycosaminoglycan sample with a test sample from the individual, under conditions that allow antibodies, if present, to bind to heparan sulfate glycosaminoglycan, thereby generating a contacted sample;

b) determining the amount of anti-heparan sulfate glycosaminoglycan antibody in the contacted sample; and c) comparing the amount of anti-heparan sulfate glycosaminoglycan antibody in the contacted sample with the amount of anti-heparan sulfate glycosaminoglycan antibody in one or more comparable negative control samples, wherein an amount of anti-heparan sulfate glycosaminoglycan antibody in the contacted sample that is greater, by a statistically significant amount, than an amount of anti-heparan sulfate glycosaminoglycan antibody in a comparable negative control sample, is indicative of the presence of at least one immune-mediated, motor-sensory polyneuropathy selected from the group consisting of: Guillain-Barré syndrome, chronic demyelinating polyneuropathy having an acute, Guillain-Barré syndrome-like onset, multifocal motor neuropathy, polyneuropathy with serum IgM M-protein, and polyneuropathy with antibodies to myelin-associated glycoprotein.

6. The method of claim 5, wherein determining the amount of the anti-heparan sulfate glycosaminoglycan antibody comprises determining the amount of antibodies that comprise IgM or IgG antibodies.

7. The method of claim 5, wherein the amount of anti-heparan sulfate glycosaminoglycan antibody is determined by enzyme-linked immunosorbent assay.

8. The method of claim 5, wherein an amount of anti-heparan sulfate glycosaminoglycan antibody in the contacted sample that is significantly greater than an amount of anti-heparan sulfate glycosaminoglycan antibody in a comparable negative control sample, is an amount that is at least about three standard deviations above an amount of anti-heparan sulfate glycosaminoglycan antibody in comparable control samples.

9. The method of claim 5, wherein the amount of anti-heparan sulfate glycosaminoglycan antibody is determined as a titer.

10. The method of claim 9, wherein the anti-heparan sulfate glycosaminoglycan antibody is IgM antibody.

11. The method of claim 10, wherein the titer of anti-heparan glycosaminoglycan antibody in the contacted sample is equal to, or greater than, about 5,000 above the titer of anti-heparan sulfate glycosaminoglycan antibody in the comparable negative control sample.

12. The method of claim 5, wherein the heparan sulfate glycosaminoglycan sample comprises acetylated heparan sulfate glycosaminoglycan.

13. A method of diagnosing in an individual the presence of at least one immune-mediated, motor-sensory polyneuropathy selected from the group consisting of: Guillain-Barré syndrome, chronic demyelinating polyneuropathy having an acute, Guillain-Barré syndrome-like onset, multifocal motor neuropathy, polyneuropathy with serum IgM M-protein, and polyneuropathy with antibodies to myelin-associated glycoprotein, the method comprising the steps of:
  a) contacting a sample of a protein having a heparan sulfate glycosaminoglycan chain, with a test sample from the individual, under conditions that allow antibodies, if present, to bind to heparan sulfate glycosaminoglycan, thereby generating a contacted sample;
  b) determining the amount, in the contacted sample, of antibody that binds to the protein having a heparan sulfate glycosaminoglycan chain; and
  c) comparing the amount with the amount, in one or more comparable negative control samples, of antibody that binds to protein having a heparan sulfate glycosaminoglycan chain,
  wherein the amount, in the contacted sample, of antibody that binds to the protein having a heparan sulfate glycosaminoglycan chain, that is statistically significantly greater than the amount, in a comparable negative control sample, of antibody that binds to the protein having a heparan sulfate glycosaminoglycan chain, is indicative of the presence of at least one immune-mediated, motor-sensory polyneuropathy selected from the group consisting of: Guillain-Barré syndrome, chronic demyelinating polyneuropathy having an acute, Guillain-Barré syndrome-like onset, multifocal motor neuropathy, polyneuropathy with serum IgM M-protein, and polyneuropathy with antibodies to myelin-associated glycoprotein.

14. A method of diagnosing Guillain-Barré syndrome in an individual, comprising the steps of:
  a) contacting a heparan sulfate glycosaminoglycan sample with a test sample from the individual, under conditions that allow antibodies, if present, to bind to heparan sulfate glycosaminoglycan, thereby generating a contacted sample; and
  b) comparing the amount of anti-heparan sulfate glycosaminoglycan antibody comprising IgG antibody in the contacted sample with a reference amount, wherein the reference amount is an amount of anti-heparan sulfate glycosaminoglycan antibody that is at least about three standard deviations greater than the amount of anti-heparan sulfate glycosaminoglycan antibody in comparable negative control samples,
  wherein an amount of anti-heparan sulfate glycosaminoglycan antibody comprising IgG antibody in the contacted sample that is equal to, or greater than, the reference amount, is indicative of the presence of Guillain-Barré syndrome.

15. A method of diagnosing Guillain-Barré syndrome in an individual, comprising the steps of:
  a) contacting a heparan sulfate glycosaminoglycan sample with a test sample from the individual, under conditions that allow antibodies, if present, to bind to heparan sulfate glycosaminoglycan, thereby generating a contacted sample;
  b) determining the amount of anti-heparan sulfate glycosaminoglycan antibody comprising IgG antibody in the contacted sample; and
  c) comparing the amount of anti-heparan sulfate glycosaminoglycan antibody comprising IgG antibody in the contacted sample with the amount of anti-heparan sulfate glycosaminoglycan antibody comprising IgG antibody in one or more comparable negative control samples,
  wherein an amount of anti-heparan sulfate glycosaminoglycan antibody comprising IgG antibody in the contacted sample that is greater, by a statistically significant amount, than an amount of anti-heparan sulfate glycosaminoglycan antibody comprising IgG antibody in a comparable negative control sample, is indicative of Guillain-Barré syndrome.

16. The method of claim 15, wherein the amount of anti-heparan sulfate glycosaminoglycan antibody comprising IgG antibody is determined by enzyme-linked immunosorbent assay.

17. The method of claim 15, wherein an amount of anti-heparan sulfate glycosaminoglycan antibody comprising IgG antibody in the contacted sample that is statistically significantly greater than an amount of anti-heparan sulfate glycosaminoglycan antibody in a comparable negative control sample, is an amount that is at least about three standard deviations above an amount of anti-heparan sulfate glycosaminoglycan antibody in a comparable negative control sample.

18. The method of claim 15, wherein the amount of anti-heparan sulfate glycosaminoglycan antibody comprising IgG antibody is determined as a titer.

19. The method of claim 15, wherein the titer of anti-heparan sulfate glycosaminoglycan antibody in the contacted sample is equal to, or greater than, about 12,000 above the titer of anti-heparan sulfate glycosaminoglycan antibody in the comparable negative control sample.

20. A method of diagnosing Guillain-Barré syndrome in an individual, comprising the steps of:
- a) contacting a sample of a protein having a heparan sulfate glycosaminoglycan chain, with a test sample from the individual, under conditions that allow antibodies, if present, to bind to heparan sulfate glycosaminoglycan, thereby generating a contacted sample;
- b) determining the amount, in the contacted sample, of antibody comprising IgG antibody that binds to the protein having a heparan sulfate glycosaminoglycan chain; and
- c) comparing the amount of antibody comprising IgG antibody that binds to the protein having a heparan sulfate glycosaminoglycan chain with the amount, in at least one comparable negative control sample, of antibody comprising IgG antibody that binds to protein having a heparan sulfate glycosaminoglycan chain, wherein the amount, in the contacted sample, of antibody comprising IgG antibody that binds to the protein having a heparan sulfate glycosaminoglycan chain, that is statistically significantly greater than the amount, in the comparable negative control sample(s), of antibody comprising IgG antibody that binds to the protein having a heparan sulfate glycosaminoglycan chain, is indicative of the presence of Guillain-Barré syndrome.

* * * * *